United States Patent
Nguyen

(10) Patent No.: US 10,827,659 B2
(45) Date of Patent: Nov. 3, 2020

(54) PERSONAL MICROWAVE AUTOCLAVE AND PROCESS USING THE SAME FOR STERILIZING N95 MASKS

(71) Applicant: Trong D Nguyen, Sacramento, CA (US)

(72) Inventor: Trong D Nguyen, Sacramento, CA (US)

( * ) Notice: Subject to any disclaimer, the term of this patent is extended or adjusted under 35 U.S.C. 154(b) by 0 days.

(21) Appl. No.: 16/858,502

(22) Filed: Apr. 24, 2020

(65) Prior Publication Data

US 2020/0267876 A1    Aug. 20, 2020

Related U.S. Application Data

(63) Continuation-in-part of application No. 14/953,398, filed on Nov. 29, 2015, now Pat. No. 9,618,130.

(51) Int. Cl.
| | |
|---|---|
| *H05K 9/00* | (2006.01) |
| *A61L 2/07* | (2006.01) |
| *A61L 2/12* | (2006.01) |
| *A61L 2/00* | (2006.01) |

(52) U.S. Cl.
CPC .......... *H05K 9/0056* (2013.01); *A61L 2/0064* (2013.01)

(58) Field of Classification Search
CPC ............ A61L 2/07; A61L 2/12; H05K 9/0056
See application file for complete search history.

(56) References Cited

U.S. PATENT DOCUMENTS

| | | | | |
|---|---|---|---|---|
| 2,839,073 A | ‡ | 6/1958 | Marsh | F16K 15/202 137/232 |
| 3,159,176 A | ‡ | 12/1964 | Russell | B60T 11/28 137/49 |
| 3,405,838 A | ‡ | 10/1968 | Preisendanz | B65D 83/70 220/20 |
| 3,517,682 A | ‡ | 6/1970 | Smith | F16K 15/202 137/223 |
| 3,753,651 A | | 8/1973 | Boucher | |
| 3,880,187 A | ‡ | 4/1975 | Kneusel | B65D 83/70 137/84 |
| 3,926,556 A | | 12/1975 | Boucher | |
| 3,941,149 A | ‡ | 3/1976 | Mittleman | A61M 39/24 137/49 |

(Continued)

FOREIGN PATENT DOCUMENTS

| | | |
|---|---|---|
| EP | 1435245 A1 | 7/2004 |
| JP | 2001009009 A | 1/2001 |
| WO | WO-1998008748 A ‡ | 3/1998 |

OTHER PUBLICATIONS

Foodsaver containers, web site, www.foodsaver.com/accessories-and-parts/containers/, Oct. 2015.‡

(Continued)

*Primary Examiner* — Kevin Joyner
(74) *Attorney, Agent, or Firm* — Ernesto Garcia

(57) ABSTRACT

An autoclave including a Faraday cage, which when placed in a microwave oven sterilizes N95 masks or any other metal surgical devices through pressurized steam. The Faraday cage prevents metal inside the cage from arching when inside the microwave oven. Pressure build up occurs inside a container, which includes an umbrella valve. The container encloses the Faraday cage, which is adjustable to fit many sized objects.

18 Claims, 3 Drawing Sheets

(56) References Cited

U.S. PATENT DOCUMENTS

| | | | | |
|---|---|---|---|---|
| 4,077,429 A ‡ | 3/1978 | Kimball | F16K 24/00 | 137/58 |
| 4,181,145 A ‡ | 1/1980 | Mitchell | F16D 65/18 | 137/49 |
| 4,288,674 A | 9/1981 | Councell | | |
| 4,349,035 A ‡ | 9/1982 | Thomas | A61B 5/15003 | 600/57 |
| 4,400,357 A | 8/1983 | Hohmann | | |
| 4,434,810 A ‡ | 3/1984 | Atkinson | F16K 15/147 | 137/49 |
| 4,443,219 A ‡ | 4/1984 | Meisch | A61F 5/4405 | 604/256 |
| 4,490,597 A | 12/1984 | Mengel | | |
| 4,503,307 A | 3/1985 | Campbell | | |
| 4,614,514 A | 9/1986 | Carr et al. | | |
| 4,671,935 A | 6/1987 | Rohrer | | |
| 4,823,831 A ‡ | 4/1989 | Jaw | F16K 15/202 | 137/223 |
| 4,861,956 A | 8/1989 | Courneya | | |
| 4,924,899 A ‡ | 5/1990 | Po | A63H 3/06 | 137/232 |
| 4,926,908 A ‡ | 5/1990 | Dschida | F16K 15/147 | 137/59 |
| 4,944,732 A ‡ | 7/1990 | Russo | A61J 15/0015 | 604/105 |
| 5,007,449 A ‡ | 4/1991 | Marrone, II | F16K 15/185 | 137/223 |
| 5,019,344 A | 5/1991 | Kutner et al. | | |
| 5,031,785 A ‡ | 7/1991 | Lemme | B65B 31/047 | 141/65 |
| 5,039,495 A | 8/1991 | Kutner et al. | | |
| 5,083,581 A ‡ | 1/1992 | Jaw | F16K 15/202 | 137/223 |
| 5,119,842 A ‡ | 6/1992 | Jaw | B60P 7/065 | 137/232 |
| 5,125,897 A ‡ | 6/1992 | Quinn | A61J 15/0015 | 604/175 |
| 5,209,902 A | 5/1993 | Matthews | | |
| 5,248,478 A | 9/1993 | Kutner et al. | | |
| 5,249,598 A ‡ | 10/1993 | Schmidt | B60K 15/03519 | 137/49 |
| 5,336,203 A ‡ | 8/1994 | Goldhardt | A61J 15/0038 | 604/247 |
| 5,343,889 A ‡ | 9/1994 | Jaw | F16K 15/202 | 137/232 |
| 5,417,941 A | 5/1995 | McNulty | | |
| 5,535,900 A ‡ | 7/1996 | Huang | B65B 31/047 | 137/52 |
| 5,607,612 A | 3/1997 | Held | | |
| 5,645,748 A * | 7/1997 | Schiffmann | A61L 2/12 | 219/710 |
| 5,759,486 A | 6/1998 | Peterson | | |
| 5,858,303 A | 1/1999 | Schiffmann | | |
| 5,871,702 A | 2/1999 | Kutner et al. | | |
| 5,941,391 A ‡ | 8/1999 | Jury | B65B 31/047 | 137/22 |
| 5,944,211 A ‡ | 8/1999 | Woodnorth | B65D 81/2038 | 220/203.13 |
| 5,997,503 A ‡ | 12/1999 | Willis | A61J 15/0015 | 604/103.07 |
| 5,997,546 A ‡ | 12/1999 | Foster | A61J 5/0042 | 604/96.01 |
| 6,019,746 A ‡ | 2/2000 | Picha | A61J 15/0015 | 604/175 |
| 6,039,921 A | 3/2000 | Boucher | | |
| 6,164,314 A ‡ | 12/2000 | Saputo | F16K 15/202 | 137/232 |
| 6,419,670 B1 ‡ | 7/2002 | Dikeman | A61J 5/0015 | 604/533 |
| 6,453,940 B1 ‡ | 9/2002 | Tipton | F04B 53/1092 | 137/49 |
| 6,460,560 B1 ‡ | 10/2002 | Weinheimer | F16K 15/205 | 137/232 |
| 6,637,321 B2 ‡ | 10/2003 | Wang | A23L 3/0155 | 215/22 |
| 6,646,241 B1 | 11/2003 | Varma | | |
| 6,814,639 B1 ‡ | 11/2004 | Peterson | F16K 15/205 | 441/41 |
| 6,878,130 B2 ‡ | 4/2005 | Fournie | A61J 15/0015 | 604/100.01 |
| 6,908,449 B2 ‡ | 6/2005 | Willis | A61F 5/445 | 604/103.06 |
| 6,990,994 B2 ‡ | 1/2006 | Reeb | F16K 15/205 | 137/223 |
| 7,048,136 B2 ‡ | 5/2006 | Havens | B65D 51/1644 | 206/52 |
| 7,051,753 B1 ‡ | 5/2006 | Caires | F16K 15/205 | 137/232 |
| 7,108,147 B2 ‡ | 9/2006 | Cheung | F16K 17/28 | 137/533.31 |
| 7,124,489 B2 ‡ | 10/2006 | Triebes | A61M 25/001 | 264/239 |
| 7,243,676 B2 ‡ | 7/2007 | Bailey | A61M 39/24 | 137/49 |
| 7,892,209 B2 ‡ | 2/2011 | Harand | A61M 16/0463 | 604/167.01 |
| 7,921,874 B2 ‡ | 4/2011 | Tekulve | F16K 15/147 | 137/513.3 |
| 8,142,394 B1 ‡ | 3/2012 | Rotella | A61J 15/0015 | 604/100.03 |
| 8,146,765 B2 ‡ | 4/2012 | Chen | B65D 43/022 | 215/26 |
| 8,337,470 B2 ‡ | 12/2012 | Prasad | A61M 39/223 | 137/49 |
| 8,413,857 B2 ‡ | 4/2013 | Johnson | B65D 75/5877 | 222/105 |
| 8,579,870 B2 ‡ | 11/2013 | Willis | A61F 5/445 | 604/167.04 |
| 8,584,695 B2 ‡ | 11/2013 | Lau | F16K 15/202 | 137/232 |
| 9,033,930 B2 ‡ | 5/2015 | Griffith | A61J 15/0065 | 604/174 |
| D735,525 S ‡ | 8/2015 | Nguyen | F04B 53/127 | D23/233 |
| 9,126,014 B2 ‡ | 9/2015 | Yamoto | A61J 5/0042 | |
| 9,453,453 B2 ‡ | 9/2016 | Nakajima | F01P 1/06 | |
| 10,151,396 B2 | 12/2018 | Nguyen | | |
| 2002/0077603 A1 ‡ | 6/2002 | Willis | A61J 15/0042 | 604/246 |
| 2003/0045841 A1 ‡ | 3/2003 | Palcisko | A61J 15/0092 | 604/256 |
| 2003/0150487 A1 ‡ | 8/2003 | Wu | F16K 15/20 | 137/223 |
| 2004/0103987 A1 ‡ | 6/2004 | Triebes | A61M 25/1036 | 156/294 |
| 2005/0109398 A1 ‡ | 5/2005 | Huang | F16K 15/147 | 137/223 |
| 2005/0187524 A1 ‡ | 8/2005 | Willis | A61F 5/445 | 604/256 |
| 2007/0074760 A1 ‡ | 4/2007 | Wu | A47C 27/082 | 137/223 |
| 2007/0276356 A1 ‡ | 11/2007 | Downing | A61M 39/12 | 604/535 |
| 2008/0119793 A1 ‡ | 5/2008 | Adams | A61J 15/0042 | 604/174 |
| 2008/0185061 A1 ‡ | 8/2008 | Fisk | F16K 15/147 | 137/846 |
| 2008/0196768 A1 ‡ | 8/2008 | Steffan | F16L 55/115 | 137/232 |
| 2009/0139582 A1 ‡ | 6/2009 | Franta | F16K 15/202 | 137/232 |
| 2010/0057013 A1 ‡ | 3/2010 | Harada | A61J 15/0015 | 604/175 |
| 2010/0176152 A1 ‡ | 7/2010 | Johnson | B65D 75/5877 | 222/92 |
| 2012/0161044 A1 ‡ | 6/2012 | Chen | B65D 81/2038 | 251/61 |

(56) References Cited

U.S. PATENT DOCUMENTS

| | | | | |
|---|---|---|---|---|
| 2015/0037113 A1 ‡ | 2/2015 | Maness | ............... | F16K 15/063 410/119 |
| 2016/0003365 A1 ‡ | 1/2016 | Park | ................. | F61K 15/148 220/212.5 |
| 2016/0186874 A1 ‡ | 6/2016 | Lin | ................. | F16K 15/202 137/232 |

OTHER PUBLICATIONS

Vacuumsaver, web site, www.vacuumsaver.com/product/?type_id=7, Oct. 2015.‡

Minivalve combination valves, web site, www.minivalve.com/newsite/index.php/en/by-type/duckbill-umbrella-combination-valves/how-they-work, Oct. 2015.‡

Vernay Flow Controls, web site, www.vernay.com/Markets/Medical/Product-Categories/Combination-Valves.aspx, Oct. 2015.‡

Vacuware, web site, vacuware.com, Oct. 2015.‡

Kinetic Premier containers, web site, www.kinetic-cookware.com/premier, Oct. 2015.‡

Vacuvin storage containers, web site, vacuvin.com/286/357/Vacuum-Container-(Small-0,65L), Oct. 2015.‡

Microjet: L'autoclave le plus rapide du monde, technical sheet brochure, Enbio, Oct. 25, 2016.

"Covid-19 Pandemic: Face Mask Disinfection & Sterilization for Viruses", Scott Mechler, Apr. 10, 2020.

"Doctors scramble for best practices onreusing medical masks during shortage", Rafi Letzter, Mar. 23, 2020.

"Does Microwaving Masks Disinfect Viruses?", Paddy Robertson, Apr. 3, 2020.

Egg Boiler #64802, Product Brochure, https://www.nordicware.com/egg-boiler, Aug. 15, 2019.

"Evaluation of Five Decontamination Methods for Filtering Facepiece Respirators", Oxford Journals, Dennis J. Viscus, Oct. 4, 2009.

"Evaluation of Microwave Steam Bags for the Decontamination of Filtering Facepiece Respirators", PLOS, Edward M. Fisher, Apr. 15, 2011.

\* cited by examiner
‡ imported from a related application

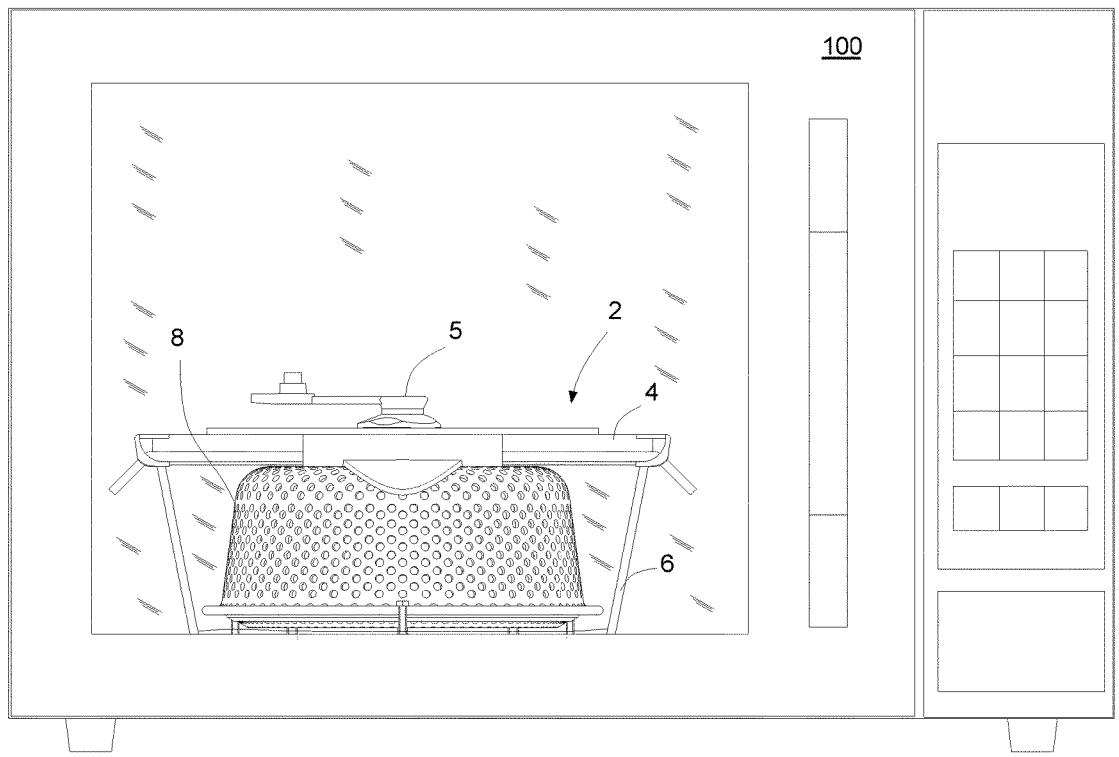
Figure 1
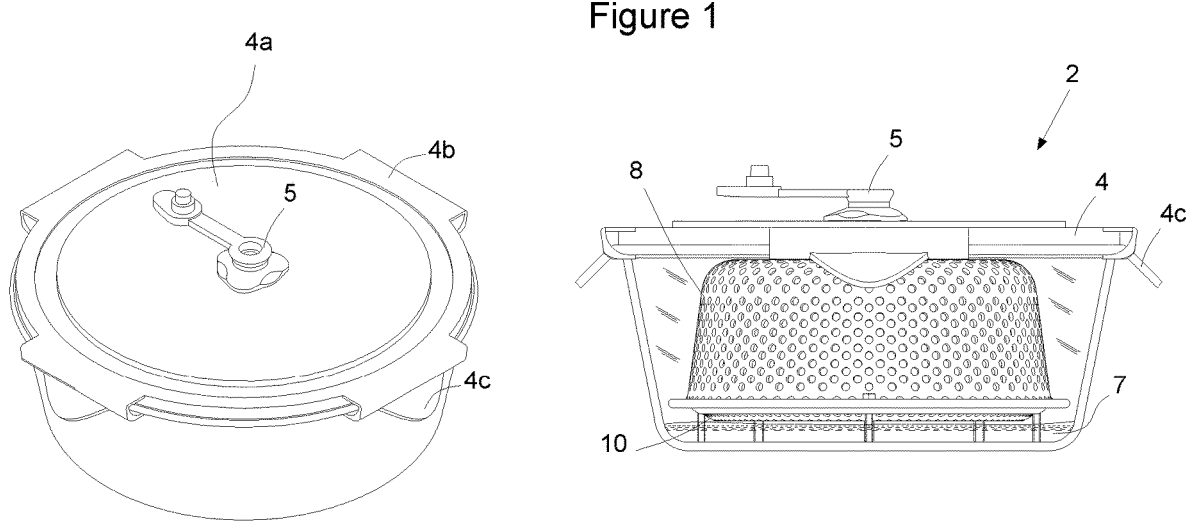
Figure 2
Figure 3

PERSONAL MICROWAVE AUTOCLAVE AND PROCESS USING THE SAME FOR STERILIZING N95 MASKS

FIELD OF THE INVENTION

The present invention relates to methods of sterilizing small metallic and non-metallic household items and medical tools by steam pressure generated by ordinary consumer microwave ovens for personal uses.

BACKGROUND OF THE INVENTION

It's well known that microwave ovens are universally popular appliance for cooking, heating and reheating food at home and in the workplace around the world. Food contains water, so during cooking the microwave energy causes the water molecules to agitate at over two thousand million times per second. This creates heat and the food is cooked, thawed or reheated. When enough microwave energy is applied, water boils and turns into hot steam. At the same time, microwave energy is reflected by metal and other metallic materials and therefore contained inside the oven's sealed metal box. However, it passes through non-metallic materials, which do not contain moisture such as glass, china, paper and plastics. The oven's glass door has an embedded layer of perforated metal screen with small holes to block the microwave energy while allows light to pass through.

Microwave ovens are generally accepted as safe. They are quite affordable to purchase and operate. It is fast and convenient to cook and heat food or beverages using microwave ovens. Also, microwave ovens are easy to use and control the cooking by time and power levels.

There are however well-accepted limitations in the ways microwave ovens are used, for example:
1. The container of food to be cooked in a microwave must be non-metallic because metallic containers could become extremely hot or cause arching;
2. The container's lid should not be sealingly closed so:
   a. During cooking, the generated steam is released and not built up excessively to explosive results; or
   b. After cooking, strong vacuum is not created as the container and the food are cooled down making it difficult or impossible to remove the lid;
3. There should not be any pointy small metallic objects such as a fork present inside the microwave during cooking as dangerous arching will occur at the tips of fork's tines; and,
4. The temperature of the cooked food is not distributed uniformly as the microwave energy only heats about ½" deep on the food surface exposed directly to the microwave beams. The interior and the "hidden" sides of the food may not be as hot. Many modern microwaves resort to having a turntable to alleviate this uneven cooking.

In December 2019, a new respiratory acute syndrome caused by a novel coronavirus was discovered in Wuhan, Hubei Province of China. The World Health Organization (WHO) named this coronavirus disease, COVID-19 and the virus that causes it, SARS-CoV-2, hence referred to as COVID-19 virus. Most people infected with this virus will experience mild to moderate respiratory illness and recover without requiring special treatment. Older people, and those with underlying medical problems like cardiovascular disease, diabetes, chronic respiratory disease, and cancer are more likely to develop serious illness. The mortality rate of all accountable infected people is estimated to be between 1-3% at this time (April 2020). COVID-19 virus spreads primarily through droplets of saliva or discharge from the nose when an infected person coughs or sneezes. The U.S. National Academy of Science reported on April 2 that the novel coronavirus can spread through the air—not just via the large droplets emitted in a cough or sneeze, but also by breathing. Additionally, scientists found that COVID-19 virus detectable in aerosols for up to three hours, up to four hours on copper, up to 24 hours on cardboard and up to two to three days on plastic and stainless steel. These findings suggest that people may acquire the virus through the air and after touching contaminated objects. It was also discovered that pre-symptomatic patients unwittingly shed COVID-19 virus at high rate for several days before common symptoms include fever, dry cough, and shortness of breath occur. There is no known vaccine or specific antiviral treatment for this disease at this time. So, it spreads rapidly throughout the world. The only ways to slow down this outbreak are by containment with social distancing, testing to identify infected persons and treating infected patients with supportive care.

On Jan. 20, 2020, the WHO declared COVID-19 outbreak to be a Public Health Emergency of International Concern and recognized it as a pandemic on March 11th. As the rate of infections and mortality accelerated exponentially, by March $31^{st}$, a third of the global population is on coronavirus lockdown with travel restrictions and closure of all non-essential activities and businesses. The sudden rapid spreading of this outbreak creates a severe global shortage of personal protection equipment (PPE) needed in hospitals and healthcare facilities such as surgical masks, N95 masks, medical face shields and gowns. Although PPEs are normally designed for one-time use, their shortages force the medical professionals and home caregivers of infected family members to re-use them multiple times and days. The situation is so dire that on March $30^{th}$ White House Coronavirus Daily Briefing, President Donald Trump called for the development of simple effective methods to sterilize surgical and N95 masks to re-use and alleviate their shortages.

In response to this call-to-action, an effective and rapidly deployable autoclave was invented to sterilize disposable filtering facepiece respirators (FFRs) such as surgical and N95 masks with moist pressure steam using microwave ovens. In 2006, the US National Academy of Sciences published the book *Reusability of Facemasks during an Influenza Pandemic: Facing the Flu* (2006) in which they reported that it is physically possible for FFRs to be used repeatedly by the same wearer until it becomes damaged, interferes with breathing, or is visibly soiled. Dry heat and moist heat are considered acceptable for sterilizing FFRs in crisis or emergency. In 2011, The US National Center for Biotechnology Information concluded that tests using microwave steam bags retain above 95% filtration performance efficiency of the treated FFRs while provide 99.9% effectiveness for inactivating pathogenic virus bacteriophage MS2. Although there is a well of prior art in the field of sterilization using microwave technology, there is no simple solutions for sterilizing metal parts or plastic parts with metal components using home microwave ovens.

The steam sterilizer of the present invention, hereafter referred to as personal microwave autoclave, is designed for home microwave ovens and intended primarily to sterilize the user's own items for extended uses. The challenges of this microwave autoclave invention are generating sufficient steam pressure safely and dealing with the metal wires in the nose bridge fittings of these masks, which could get hot enough to ignite them. The personal microwave autoclave of the present invention is significantly different from all existing microwave sterilizers and microwave steam bags using home microwave ovens for plastic baby bottles on the market in that it uses pressure steam and can sterilize items with metal components.

SUMMARY OF THE INVENTION

The present invention describes an affordable and easy-to-use personal microwave autoclave designed to quickly sterilize FFRs such as surgical mask, N95 masks, metallic medical tools and any small hand tools containing metallic and non-metallic components using pressure steam generated in any common consumer microwave oven. It is the intension of this present invention to alleviate the global shortage of surgical and N95 masks by sterilizing them for re-use by their owners multiple times in hospitals, clinics, essential businesses opened during coronavirus lockdown and million homes with infected family member. The microwave autoclave of the present invention is also suitable for safely sterilizing metal tools commonly used in beauty parlors and nail salons. Ultimately, the present invention would make the already popular microwave ovens even more versatile for heating products with only pressure steam generated by the microwave energy but not directly by it.

The present invention describes a personal microwave autoclave using a common home microwave oven suitable for sterilizing any small metal and non-metal combustible articles with moist pressure steam. The personal microwave autoclave is used in three typical phases of an autoclave process namely:

1. Conditioning Phase: Air inhibits sterilization and should be removed from the chamber during the first phase of the sterilization cycle known as conditioning. The air can be actively removed from the chamber using a manual or electric vacuum pump. Air can also be passively removed by dilution and displacement with the steam generated during the beginning phase of the autoclave process;
2. Exposure Phase: After the air is removed, the cycle enters the exposure phase and items are held at the sterilization temperature for a fixed amount of time required to sterilize them; and,
3. Depressure Phase: During the final phase of the cycle, steam is removed by condensation, depressurizing the vessel and allowing the sterilized items to be removed.

The personal microwave autoclave of the present invention consists of the following components:

1. An oven safe glass container made of silica, soda ash, limestone and other natural components.
2. A sealable plastic lid for the glass container which has a single hole at its center to receive the valve described below.
3. A multi-functional valve for injecting air or vacuuming air out from a closed volume of the above glass container. The valve includes a duckbill with a slit at one end that can be further sealed with a tethered plug that fits into an opened nipple at the other end. As such the valve of the present invention can be reverted to a one-way valve whenever the duckbill is closed by the tethered plug. The valve also incorporates a footing that provides clearance to the duckbill as one injects air or vacuums the closed container. The duckbill further features opposed tapered outside surfaces to assist in providing radial forces to close the slit to maintain inside pressure even without the tethered plug in place. The instant valve includes at least one axial passageway in flow with a radial passageway partly under a collapsible flap to let air escape as one vacuums the closed container. When the nipple is pressed sideways, at least one of the flaps will collapse and break the vacuum. Without the tether plug in place, the valve is envisioned to allow external air to enter the container through the duckbill automatically as sufficient negative pressure developed inside. When the tether plug is in place, the valve becomes a one-way valve and can be used to vacuum the air from inside the container;
4. An opened-end dome made with $\frac{1}{8}$"-hole perforated stainless steel or aluminum sheet acting as an electromagnetic shield box or a Faraday cage (so named after physicist Michael Faraday who invented it in 1836) to block microwave energy to penetrate its interior but allows steam to pass through. The perforated holes on this dome are sized to be sufficiently small to block the 2.45 Ghz wavelength of typical microwave wave in home microwave ovens. This Faraday cage, hereafter referred to as Faraday dome according to the present invention, fits inside the glass container, standing vertically on its open bottom, and is large enough to accommodate the object to be sterilized inside;
5. Another flat bottom member of round perforated stainless steel sheet with standoffs to fits inside the Faraday dome and, together with it, forms a completely shielded cage. In certain instant, this bottom member of the Faraday dome could just be a sufficiently deep layer of water (as described below) to absorb and block microwave energy from entering inside the cage. In either iterations, the interior of the Faraday dome is substantially shielded from the microwave energy while freely receiving hot pressure steam generated by the microwave energy applied on the layer of water at the bottom of the sealed glass container;
6. An optional manual or suitable electric vacuum pump to remove air from the sealed glass container; and,
7. A $\frac{1}{2}$" layer of distilled water at the bottom of the glass container is used to absorb all the microwave energy to create moist steam and to block deflected microwave energy from the floor of microwave oven enclosure to penetrate the bottom side of the Faraday dome.

To sterilize items without embedded metal component, metallic items, or plastic items with embedded metal component using the personal microwave autoclave:

1. Fill the glass container with $\frac{1}{2}$" layer of distilled water;
2. Place a dish or a flat bottom member, of a Faraday cage in the container;
3. Place the item to be sterilized on the dish and enclose the item with a dome of the Faraday cage;
4. Place the lid on the container and close it sealingly to form a hermetically sealed container;
5. Optionally vacuum out the air with a manual or electric vacuum pump;
6. Place the personal microwave autoclave inside a microwave and close its door;
7. Set the timer for enough time at 100% power level to maintain a rapid boiling of the water for 2 minutes;
8. When the heating is done, let the personal microwave autoclave sit for 1 minute for the heat to penetrate all part of the item and the temperature and pressure subside. A slight vacuum is developed inside the container as things cool down; and,
9. De-vacuum by pushing the multi-functional valve slightly sideways to remove the lid and then the sterilized item. Carefulness should be practiced, as everything is very hot at this time.

Operational principle of the Persona icrowave Autoclave of the present invention are as follows:

Conditioning Phase: Removal of air is either actively carried out by using a manual or electric vacuum pump before heating or passively as water turns into pressure steam by the microwave energy inside the sealed glass container during the initial phase of steam generating to displace the air through the bi-directional valve;

Exposure Phase: As more water turns into higher pressure steam, the reversible di-directional valve releases excessive steam pressure and therefore maintains a sustainable heat and pressure level for effective sterilization. While microwave energy cannot penetrate the Faraday cage to excessively heat up metallic components, steam pressure is unobtrusively distributed throughout the inside of the container. This steam pressure is created by moist and air-free steam which is more efficient for sterilization; and, Depressure Phase: When the heating cycle ends, the sealed glass container and its content are cooling down very slowly creating a vacuum in the process. This vacuum helps deliver residual heat to any cooler spots on or deep inside the item to be sterilized.

BRIEF DESCRIPTION OF THE DRAWINGS

FIG. 1 shows a front view of a process using the autoclave of the instant invention.

FIG. 2 shows an isometric view of the autoclave shown in FIG. 1.

FIG. 3 shows a front view of the autoclave shown in FIGS. 1 and 2.

DETAIL DESCRIPTION OF THE DRAWINGS

Figure 4:
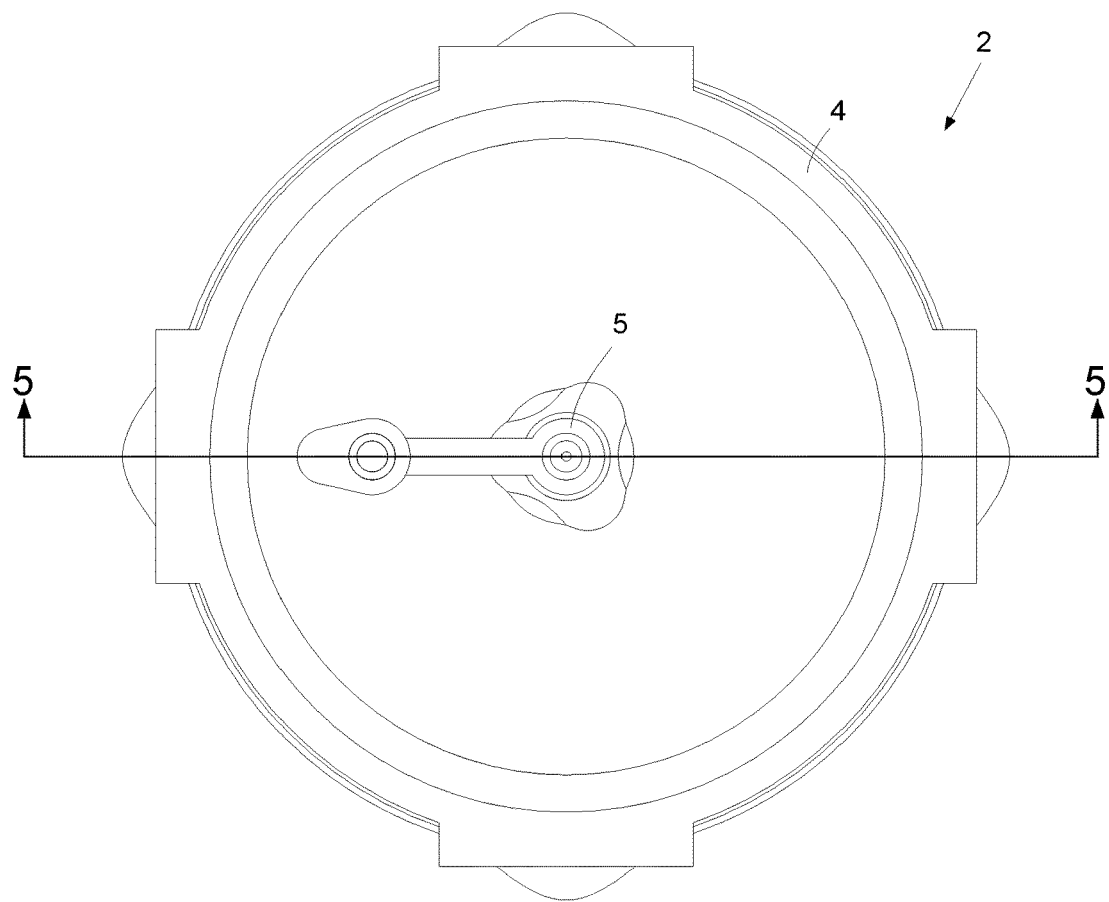
FIG. 4 shows a top view of the autoclave shown in FIG. 2.

FIG. 1 shows an autoclave 2 inside a microwave oven 100. The autoclave 2 comprises a container 6 with a lid 4. The lid 4 includes an umbrella valve 5 on top of the lid 4. The container 6 is normally made from glass but the material can be made from any other material as long it can hold pressure build up inside. As shown in FIG. 2, the lid 4 has at least one means securing means for securing the lid 4 to the container 6 and hermetically sealing the container 6. The securing means comprises a series of locking flaps 4b that allow the lid 4 to be secured to the container 6. Each flap 4b includes a projecting handle 4c that allows the user to unlock the flap 4b from the container 6. One skilled in the art would have found that there are many ways to secure a lid to a container and thus not the crux of the instant invention. An o-ring seal 4x is sandwiched between the lid 4 and the container 6, FIG. 5. The umbrella valve 5 is designed by the same applicant and disclosed in U.S. Pat. No. 10,151,396 B2, and thus hereby incorporated in reference in its entirety. The umbrella valve 5 is fixed through a hole in the lid 4 and the valve 5 has radial vents 5a, a duckbill 5b and a slit 5c.

Figure 5:
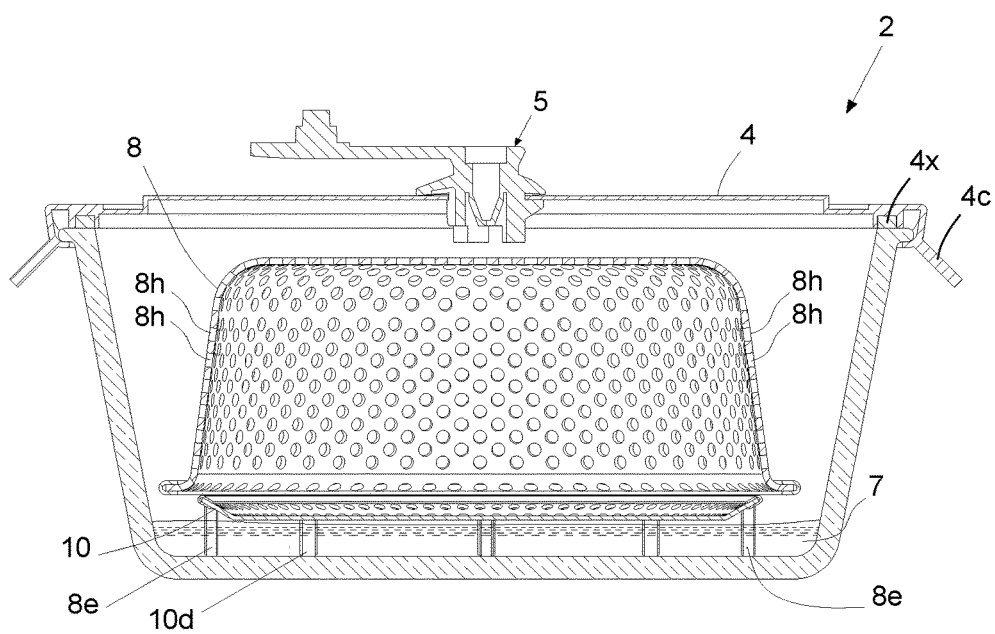
FIG. 5 shows cross-sectional view 5-5 shown in FIG. 4.
Figure 6:
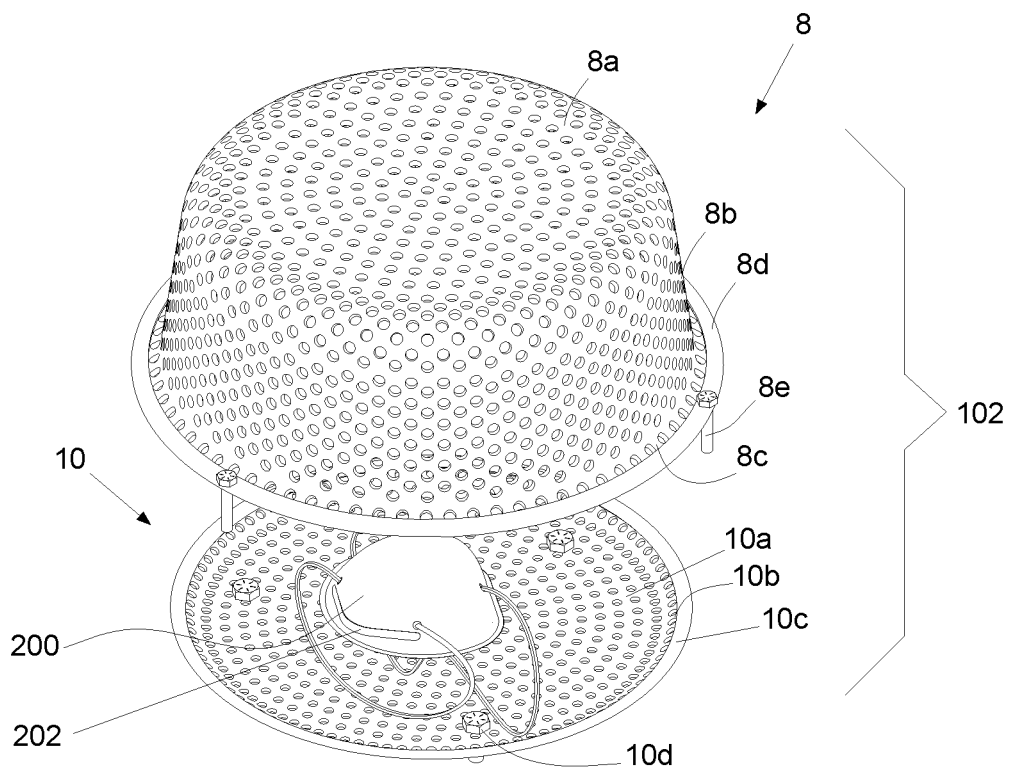
FIG. 6 shows an isometric view of the Faraday cage shown in FIG. 1-3.
Figure 7:
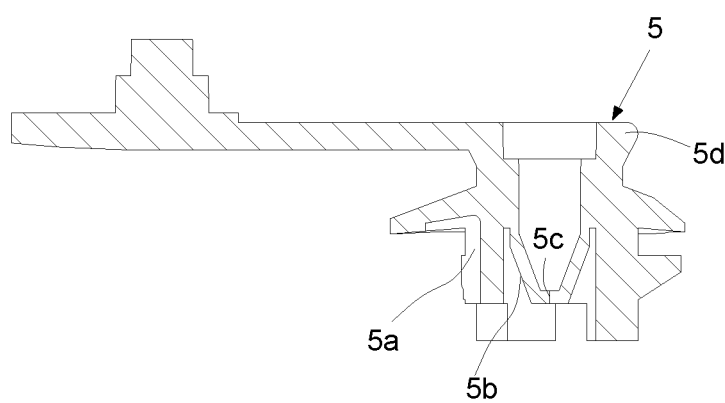
FIG. 7 shows a blown-up cross-sectional view of the valve shown in FIG. 5.

FIG. 3 shows the autoclave 2 by itself without the microwave oven 100. The autoclave 2 comprises a dome 8 perforated with a series of holes 8h so as to avoid microwaves entering inside the dome 8 when the autoclave is used in the microwave oven 100. As shown in FIGS. 5 and 6, the dome 8 has evenly distributed legs 8e that are adjustable. In this instant sample, the legs 8e are threaded fasteners that one can manually adjust to a certain preferred height. The dome 8 comprises a flat ceiling 8a, a peripheral wall 8b that terminates in a rim 8c. The flat ceiling 8a, the peripheral wall 8b and the rim 8c are all perforated. The dome 8 further includes a U-shaped border 8d so as to protect a user from sharp edges of the rim 8c since the dome 8 is made from metal such as stainless steel. The border 8d surrounds the entire rim 8c.

As shown in FIGS. 3 and 5, the dome 8 is set above a circular dish 10 so as to form a Faraday cage 102, FIG. 6. The dish 10 comprises a platform 10a that terminates at an angled rim 10b. The angled rim 10b is set at an angle of 30 degrees but of course the angle can be set at any angle. The angled rim 10b, similarly as the rim 8c, has a U-shaped border 10c so as to protect as well. The circular dish 10 is also made from metal and also has a series of feet adjusters 10d. The feet adjusters 10d are similar in shape as the legs 8e. It is envisioned that the feet adjusters 10d and legs 8e can take any other shape so as to be able to adjust the level of the dome 8 or dish 10.

FIG. 6 shows an application of the cage 102. For instance, a N95 mask 200 can be placed on the dish 10 and then enclosed with the dome container 8. It is a common design that a N95 mask 200 contains a metal strip embedded or bonded on top of a mask. The cage 102 with the mask 200 inside is set inside the glass container 6 filled with some water 7 and then closed up using the lid 4 having the umbrella valve 5. When the autoclave 2 is placed inside the microwave oven 100 and the microwave oven 100 is activated, will creates microwaves will be prevented from going inside the cage 102. The cage 102 will prevent the metal strip of the mask 200 from getting heated by the microwave and ignite the mask. As the microwave oven 100 further heats up the water 7, the water will steam up and create pressure build up inside the container 6 that at certain steam pressure will escape from the valve 5 through the vents 5a.

Microwave energy heats and boils the water into pressure steam. The umbrella valve 5 releases the built-up internal steam pressure of the container 6 when such pressure is surpassed its designed limit through the umbrella valve 5. Once sterilizing, the valve 5 allows air to enter the container 6 through the slit 5c when a vacuum is developed as the container 6 is cooling down after steaming. A residual vacuum would remain at the level dictated by the native closing force of the duckbill 5b. If any residual vacuum remains, the vacuum can be eliminated when pressing or pushing sideways on the nipple 5d so the lid 4 can be easily removed from the container 6.

It is envisioned that while a N95 mask has been disclosed as an item to be sterilized, that other items that have metal or medical surgical devices can be sterilized through steaming.

The invention claimed is:

1. An autoclave comprising a container, a lid, an umbrella valve, and a cage inside the container;
   wherein the cage consists of metal;
   wherein the umbrella valve is fixed to the lid;
   wherein the lid comprising at least one securing means for securing the lid to the container and hermetically sealing the container;
   and,
   wherein the cage comprises a perforated dome and a perforated dish.

2. The autoclave of claim 1, wherein the perforated dome comprises a ceiling, and a peripheral wall terminating into a rim.

3. The autoclave of claim 2, wherein the perforated dish comprises a platform and a rim.

4. The autoclave of claim 3, wherein the rim of the dish includes a U-shaped border enclosing the rim of the dish.

5. The autoclave of claim 2, wherein the rim includes a U-shaped border enclosing the rim.

6. The autoclave of claim 2, wherein the dome and the dish includes feet adjusters.

7. The autoclave of claim 6, wherein the feet adjusters of the dome intersect the rim of the dome.

8. The autoclave of claim 6, wherein the feet adjusters of the dish intersect the platform of the dish.

9. The autoclave of claim 1, wherein the umbrella valve includes a duckbill with a slit and a nipple to allow devaccuming and pressure stabilization.

10. The autoclave of claim 1, wherein the at least one securing means comprises a series of hinged flaps.

11. The autoclave of claim 1, wherein an o-ring is sandwiched between the lid and the container.

12. The autoclave of claim 1, wherein the umbrella valve includes radial vents.

13. An autoclave comprising a container, a lid, an umbrella valve, and a cage inside the container;
   wherein the cage consists of metal;
   wherein the umbrella valve is fixed to the lid;
   wherein the lid comprising at least one securing means for securing the lid to the container and hermetically sealing the container; and,
   wherein the cage comprises a perforated dome.

14. The autoclave of claim 13, wherein the perforated dome comprises a ceiling, a peripheral wall terminating into a rim.

15. The autoclave of claim 14, wherein the rim includes a U-shaped border enclosing the rim.

16. The autoclave of claim 13, wherein the dome includes feet adjusters through the rim.

17. A process of sterilization a metal article using an autoclave, comprising the steps of:
   placing water in a container of the autoclave;
   placing a perforated metal dish of the autoclave inside the container;
   placing the metal article on top of the metal dish;
   placing a perforated metal dome over the metal dish and metal article;
   closing the container with a lid of the autoclave to form a hermetically sealed container;
   inserting the autoclave inside a microwave oven;
   activating the microwave oven to create pressured steam inside the container to sterilize the metal article; and,
   releasing the pressured steam through radial vents of an umbrella valve fixed to the lid.

18. The process of sterilization of claim 17, further including the step of:
   atmospheric pressure entering into the container through a slit in a duckbill of the umbrella valve.

* * * * *